(12) United States Patent
Forsberg et al.

(10) Patent No.: US 8,430,906 B2
(45) Date of Patent: Apr. 30, 2013

(54) METHOD AND APPARATUS TO PROMOTE HEMOSTASIS

(75) Inventors: Andrew T. Forsberg, Minneapolis, MN (US); Anissa F. Pietrarosso, Lake in the Hills, IL (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 1425 days.

(21) Appl. No.: 11/537,317

(22) Filed: Sep. 29, 2006

(65) Prior Publication Data

US 2008/0082123 A1 Apr. 3, 2008

(51) Int. Cl.
*A61B 17/08* (2006.01)
(52) U.S. Cl.
USPC ............................ 606/213; 606/151; 606/157
(58) Field of Classification Search .................. 606/213, 606/214, 229
See application file for complete search history.

(56) References Cited

U.S. PATENT DOCUMENTS

| | | | | |
|---|---|---|---|---|
| 4,700,692 A * | 10/1987 | Baumgartner | ..................... | 600/7 |
| 5,053,046 A * | 10/1991 | Janese | ........................... | 606/215 |
| 5,222,974 A * | 6/1993 | Kensey et al. | ................. | 606/213 |
| 5,281,197 A * | 1/1994 | Arias et al. | ........................ | 604/57 |
| 5,413,571 A * | 5/1995 | Katsaros et al. | ............... | 606/213 |
| 5,531,759 A * | 7/1996 | Kensey et al. | ................. | 606/213 |
| 6,659,996 B1 * | 12/2003 | Kaldany | ......................... | 604/508 |
| 6,846,320 B2 * | 1/2005 | Ashby et al. | .................... | 606/213 |
| 6,860,895 B1 * | 3/2005 | Akerfeldt et al. | .............. | 606/215 |
| 6,862,470 B2 * | 3/2005 | Burbank et al. | ................ | 600/431 |
| 7,001,410 B2 * | 2/2006 | Fisher et al. | ................... | 606/229 |
| 7,335,220 B2 * | 2/2008 | Khosravi et al. | ............... | 606/213 |
| 2003/0050613 A1 * | 3/2003 | Hammerslag | ................. | 604/290 |
| 2003/0233120 A1 * | 12/2003 | Akerfeldt | ....................... | 606/213 |
| 2005/0085851 A1 | 4/2005 | Fiehler et al. | | |
| 2005/0107826 A1 * | 5/2005 | Zhu et al. | ....................... | 606/213 |
| 2005/0123588 A1 * | 6/2005 | Zhu et al. | ....................... | 424/443 |

* cited by examiner

*Primary Examiner* — Corrine M McDermott
*Assistant Examiner* — Alexander Orkin
(74) *Attorney, Agent, or Firm* — Holland & Hart

(57) ABSTRACT

Apparatus and methods for promoting hemostasis are provided. The apparatuses and methods have particular applicability with tissue puncture closure devices for sealing percutaneous punctures in arteries. In one embodiment, an apparatus for promoting hemostasis a tube having at least one indentation for holding a hemostatic substance. In further embodiments, the apparatus may further include a carrier tube for forming a lid for the indentation, a retractable sheath for forming a lid for the indentation, or a cover for forming a lid of the indentation. In an alternative embodiment the apparatus for promoting hemostasis comprises a suture provided with a hemostatic substance.

12 Claims, 6 Drawing Sheets

METHOD AND APPARATUS TO PROMOTE HEMOSTASIS

FIELD OF THE INVENTION

This invention relates generally to a method and apparatus to promote hemostasis, and more specifically, to a method and apparatus to promote hemostasis at the site of a suture in a tract or artery.

BACKGROUND OF THE INVENTION

Many devices are available to close a puncture or incision in an artery. Most typically, a suture and/or mechanical closure is deployed at the puncture or incision. Occasionally tract oozing occurs after the closure has been deployed. When tract oozing occurs, it is frequently necessary to apply manual compression to control the oozing.

A need exists for a method of promoting hemostasis, thereby controlling tract oozing, at the site of a mechanical closure.

BRIEF SUMMARY OF THE INVENTION

Apparatuses and methods for promoting hemostasis are provided. The apparatuses and methods have particular applicability with tissue puncture closure devices for sealing percutaneous punctures in arteries. In one embodiment, an apparatus for promoting hemostasis at the site of a vascular puncture or incision comprises a tube having at least one indentation for holding a hemostatic substance. In further embodiments, the apparatus may further include a carrier tube for forming a lid for the indentation, a retractable sheath for forming a lid for the indentation, or a cover for forming a lid of the indentation.

In a further embodiment, a tissue puncture closure device having an apparatus for promoting hemostasis is provided. The tissue puncture closure device includes a filament, an anchor, a sealing tube, and a tamping tube. The filament extends from a first end of the closure device to a second end of the closure device. The anchor is configured for insertion through the tissue wall puncture and is attached to the filament at the second end of the closure device. The sealing plug is slidably attached to the filament adjacent to the anchor. The tamping tube is configured for tamping or cinching the sealing plug toward the second end of the closure device. In various embodiments, the apparatus for promoting hemostasis comprises a hemostatic agent provided with the filament or an indentation provided on the tamping tube for holding a hemostatic agent.

While multiple embodiments are disclosed, still other embodiments of the invention will become apparent to those skilled in the art from the following detailed description, which shows and describes illustrative embodiments of the invention. As will be realized, the invention is capable of modifications in various obvious aspects, all without departing from the spirit and scope of the invention. Accordingly, the drawings and detailed description are to be regarded as illustrative in nature and not restrictive.

DETAILED DESCRIPTION OF THE INVENTION

Methods and apparatuses for promoting hemostasis, thereby controlling tract oozing, at the site of a mechanical closure are provided.

Figure 1:
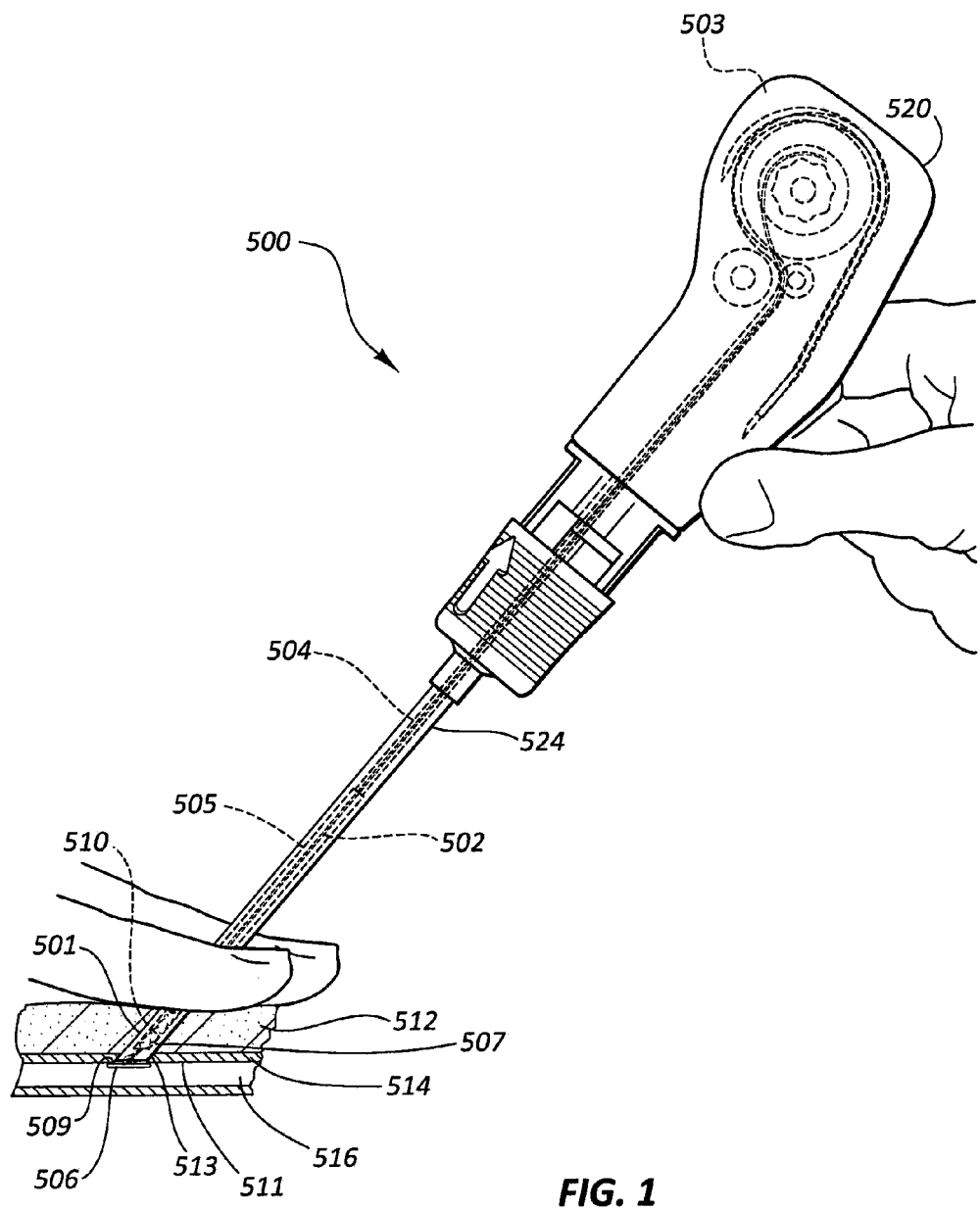
FIG. 1 illustrates a self-tamping tissue puncture closure device.

FIG. 1 illustrates a suitable tissue puncture closure device 500 for use with the present invention. Generally, the tissue puncture closure device is suitable for partial insertion into and sealing of an internal tissue wall puncture. The closure device 500 has particular utility when used in connection with intravascular procedures, such as angiographic dye injection, cardiac catheterization, balloon angioplasty and other types of recanalizing of atherosclerotic arteries, etc. as the closure device 500 is designed to cause immediate hemostasis of the blood vessel (e.g., arterial) puncture. However, it will be understood that while specific description is made to the sealing off of percutaneous punctures in arteries, such devices have wide-spread applications and can be used for sealing punctures or incisions in other types of tissue walls as well. Thus, the sealing of a percutaneous puncture in an artery is merely illustrative of one particular use of the tissue closure device 500 and methods and apparatuses to promote hemostasis.

The tissue closure device 500 includes a first or proximal end 503 and a second or distal end 507. A carrier tube 504 extends from the proximal end 503 to the distal end 507 and includes an outlet 513. The carrier tube 504 may be made of plastic or other material and is designed for insertion through a sheath designed for insertion through a percutaneous incision 501 in a tissue layer 512 and into a lumen 516. The lumen 516 defines an interior portion of a femoral artery 514. The carrier tube 504 may be provided within a sheath 524, extending from the distal end 507 towards the proximal end 503. A housing or handle 520 may be provided at the proximal end 503 for handling the tissue closure device 500. In one embodiment, the sheath 524 may extend to the handle 520.

The distal end 507 of the carrier tube 504 also includes an anchor 506 and a sealing plug 510. As shown, the anchor 506 may be an elongated, stiff, low-profile member arranged to be seated inside the artery 514 against an artery wall 511 contiguous with a puncture 513. The anchor 506 may be made of a biologically resorbable polymer. The sealing plug 510 may be formed of a compressible sponge or foam, also made of a non-hemostatic biologically resorbable material such as collagen, and may be configured in any shape so as to seal the tissue puncture 513. The sealing plug 510 and anchor 506 are connected to one another by a suture or filament 502 that is also biologically resorbable. The anchor 506, sealing plug 510, and suture 502 are collectively referred to as the "closure elements". The anchor 506 is arranged adjacent to and exterior of the distal end 507 of the sheath 524, while the sealing plug 510 is initially disposed within carrier tube 504. While the anchor 506 is shown deployed with a first surface 509 against the artery wall 511, it will be understood that initially the anchor is arranged axially along the carrier tube 504 to facilitate insertion into the lumen 516.

The suture 502 extends distally from the proximal end 503 of the closure device 500 through the carrier tube 504. The suture 502 is threaded through perforations in the sealing plug 510, through a hole in the anchor 506, and proximally through the carrier tube 504 back to the sealing plug 510. The suture 502 may be threaded through a perforation or series of perforations in the sealing plug 510. The suture 502 may also be threaded around itself to form a slip-knot. In one embodiment, the suture 502 thus connects the anchor 506 and the sealing plug 510 in a pulley-like arrangement that serves to cinch the anchor 506 and the sealing plug 510 together when the carrier tube 504 is pulled away from the anchor 506 and the sealing plug 510, sandwiching and locking the anchor and plug together and thereby sealing the tissue puncture 513.

The carrier tube 504 may also include a tamping device, such as a tamping tube 505, for tamping the sealing plug 510 along the suture 502 and against the anchor 506. In the embodiment shown, the tamping tube 505 is located within the carrier tube 504 proximal of the sealing plug 506. The tamping tube 505 is an elongated tubular member that may be rigid or flexible and formed of any suitable material. For example, according to one embodiment the tamping tube 505 is made of polyethylene. The suture 502 extends through the tamping tube 505 but is not directly connected thereto. Accordingly, the suture 502 and tamping tube 505 are free to slide past one another.

The tissue puncture closure device 500 of FIG. 1 is more fully described in U.S. Patent Publication No. 2005/0085851 for Tissue Puncture Closure Device with Automatic Tamping, published Apr. 21, 2005, herein incorporated by reference. Thus, as shown and described with reference to FIG. 1, a mechanical closure, including a suture or filament, may be deployed at an arteriotomy to close a tissue puncture. In accordance with one embodiment, the suture or filament includes a thrombogenic substance, hemostatic substance, or clot-producing agent to promote hemostasis, thereby controlling tract oozing, after deployment of the closure. Thus, in one embodiment, a suture is pre loaded with a material to promote hemostasis within the tract.

Figure 2:
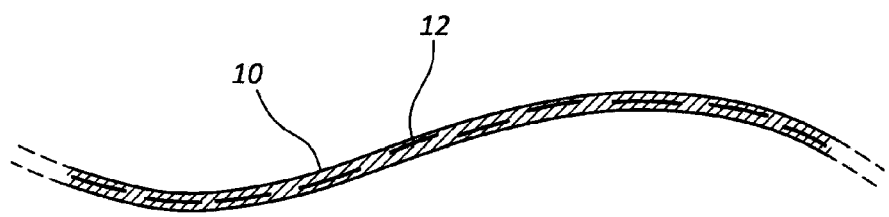
FIG. 2 illustrates a suture impregnated with a thrombogenic substance, in accordance with one embodiment.

As shown in FIG. 2, a suture 10 for deployment using the tissue puncture closure device may be injected with a thrombogenic, hemostatic, or clot-producing substance or agent 12. In this embodiment, the suture 10 is generally impregnated with the thrombogenic substance 12. Any suitable method for impregnating the suture 10 with the thrombogenic substance 12 may be used.

Figure 3:
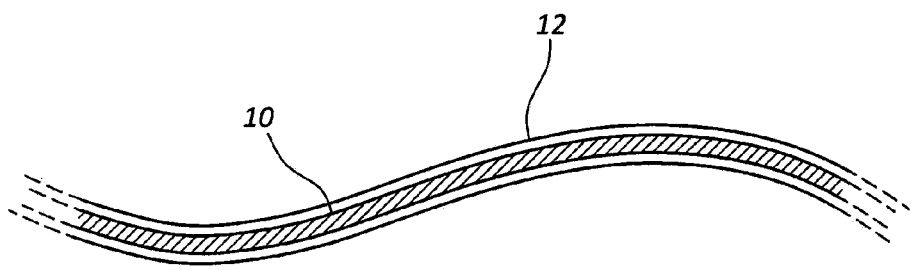
FIG. 3 illustrates a suture coated with a thrombogenic substance, in accordance with one embodiment.

Alternatively, as shown in FIG. 3, at least a portion of the suture 10 may be coated with a thrombogenic, hemostatic, or clot-producing substance or agent 12. In the embodiment of FIG. 3, the entire suture is coated with a thrombogenic substance 12. In alternative embodiments, only the portion of the suture 10 that will contact the tissue may be coated or other portion of the suture 10 may be coated. Any suitable method for coating the suture 10 with the thrombogenic substance 12 may be used. For example, the suture may be dipped in a thrombogenic substance or sprayed with a thrombogenic substance, thereby coating at least a portion of the suture with the thrombogenic substance.

In further embodiments, a thrombogenic, hemostatic, or clot-inducing agent or substance is dispensed into the tissue tract. Such dispensing of a thrombogenic substance may be used in addition to a suture provided with a thrombogenic substance or as an alternative thereto. The clot-inducing agent may be dispensed automatically at a predetermined stage in the vascular closure device deployment or may be manually deployed by the user, both described more fully below. The thrombogenic, hemostatic, or clot-inducing agent or substance may be a powder, solid, liquid, gel, or combination thereof. In one embodiment, the clot producing agent is a microporous polysaccharide hemosphere such as that used in the Stasys Patch, a topical adhesive wound dressing for the local management and control of bleeding from vascular access sites and percutaneous catheters, available commercially from St. Jude Medical of Minnetonka, Minn.

FIGS. 4 through 9 illustrate embodiments where the hemostatic, thrombogenic, or clot-inducing agent or substance is provided on a tamping tube of a vascular closure device. For example, the clot-inducing substance may be provided on the tamping tube 505 of the vascular closure device 500 of FIG. 1. Alternatively, the clot-inducing substance may be provided on the tamping tube 105 of the tissue puncture closing device 100 of FIGS. 10 and 11, described below. Further, in alternative embodiments, the hemostatic, thrombogenic, or clot-inducing agent or substance may be provided on a deployment tube other than a tamping tube.

Figure 4:
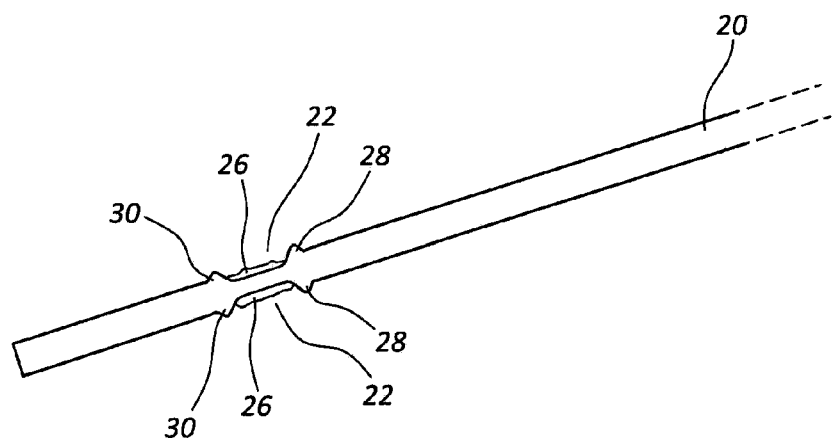
FIG. 4 illustrates a tamping tube for carrying a clot-inducing agent, in accordance with one embodiment.
Figure 5:
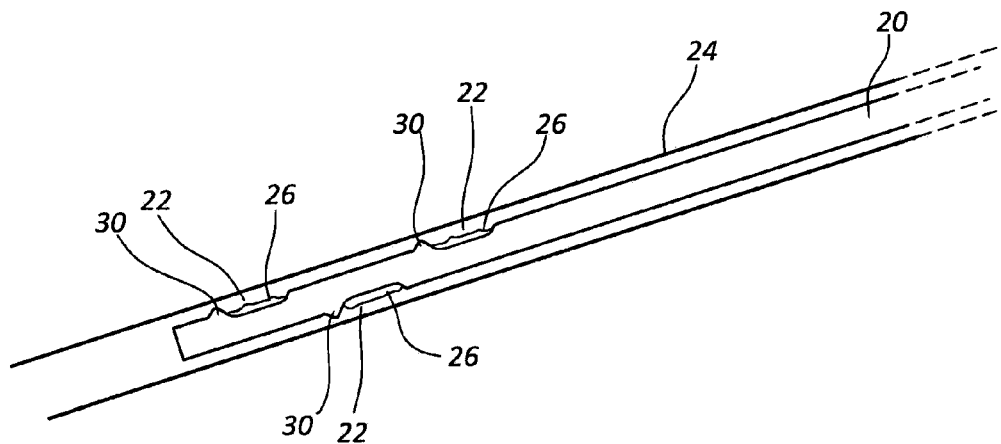
FIG. 5 illustrates tamping tube for carrying a clot-inducing agent within a carrier tube, in accordance with one embodiment.

A first embodiment for dispensing a hemostatic, thrombogenic, or clot-inducing agent or substance into the tissue tract is shown in FIGS. 4 and 5. As shown, the clot-inducing agent is provided on a tamping tube 20. FIG. 5 illustrates the tamping tube 20 within a carrier tube 24. The carrier tube 24 may be the carrier tube of the vascular closure device. The tamping tube 20 includes at least one indentation 22 along a surface thereof. The indentation 22 forms a reservoir for the hemostatic agent 26. In the embodiment of FIG. 4, two indentations 22 are shown, the indentations 22 being provided at approximately equal lateral positions along the tamping tube 20. In the embodiment of FIG. 5, three indentations 22 are shown, the indentations 22 being provided at varying lateral positions along the tamping tube 20. In alternative embodiments, only one indentation 22 may be provided.

Wipers 28, 30, or protrusions, may be provided to keep the hemostatic agent 26 in the at least one indentation 22. As shown in FIG. 4, the wipers may be provided proximal (28) and distal (30) to the indentation 22. In the embodiment of FIG. 5, the wipers 30 are provided only distal to the indentation 22. In alternative embodiments, the wipers 28 may be provided only proximal or only distal to the indentation 22. The internal diameter of the carrier tube 24 may be used as a cap for the at least one indentation 22. Thus, the carrier tube 24 may connect the proximal end of a handle 520 to the distal components such as the closure elements. The dimension of the internal diameter may be varied depending on the overall size and use of the device 500.

During tamping of the collagen, the tamping tube 20 is moved distally, thus being distally expelled from the carrier tube 24. The clot-inducing agent 26 or thrombogenic substance is exposed to the tissue tract after the distal wiper 30 or the edge of the indentation 22 passes beyond the distal end of the carrier tube 24. When the clot-inducing agent 26 is exposed, it initiates hemostasis in the tract, and acts to reduce tract oozing. As the collagen has already been partially or fully tamped, there is minimal risk of the clot-inducing agent 26 entering the femoral artery.

Figure 6:
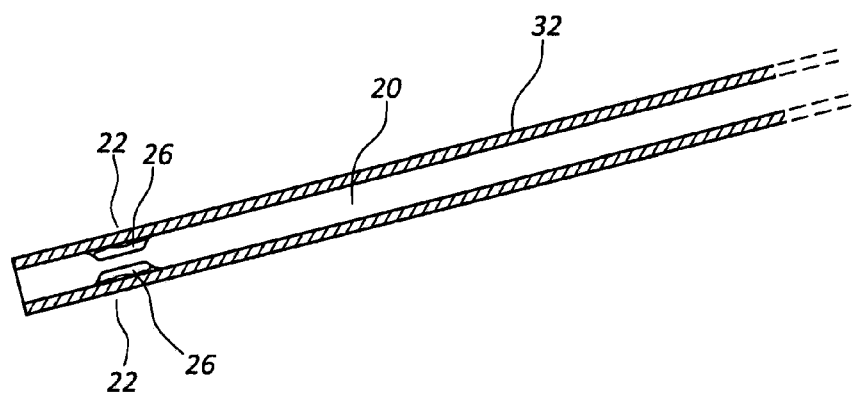
FIG. 6 illustrates a retracting sheath for dispensing a clot-inducing agent prior to deployment of the clot-inducing agent, in accordance with one embodiment.
Figure 7:
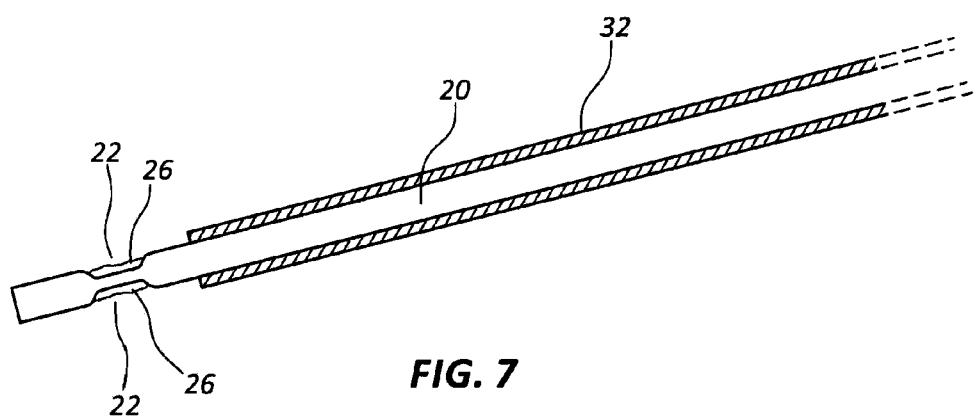
FIG. 7 illustrates the retracting sheath of FIG. 6 during or after deployment of the clot-inducing agent, in accordance with one embodiment.

FIGS. 6 and 7 illustrate a retracting sheath embodiment of a tamping tube 20 for dispensing a hemostatic, thrombogenic, or clot-inducing agent or substance. As shown, a tamping tube 20 is provided holding the clot-inducing agent 26 or thrombogenic substance and a sliding or retractable tube 32 is provided over the tamping tube 20. The tamping tube 20 includes at least one indentation 22 along a surface thereof. The indentation 22 forms a reservoir for the hemostatic agent 26. Where a plurality of indentations 22 are provided, the indentations 22 may be provided at approximately equal lateral positions along the tamping tube 20, as shown, or may be provided at varying lateral positions along the tamping tube 20. FIG. 6 illustrates the tamping tube 20 provided within the sliding or retractable tube 32 prior to deployment of the clot-inducing agent 26. After tamping is complete, the user pulls back the outer sliding tube 32, thus exposing the tissue tract to the clot-inducing agent 26 provided on the tamping tube 20. When the clot-inducing agent 26 is exposed, it initiates hemostasis in the tract, and acts to reduce tract oozing. As the collagen has already been partially or fully tamped, there is minimal risk of the agent entering the femoral artery. FIG. 7 illustrates the sliding tube 32 partially retracted from the tamping tube 20, thereby exposing the clot-inducing agent 26. Using the embodiment of FIGS. 6 and 7, the user controls if, when, and where the clot-inducing agent is deployed.

Figure 8:
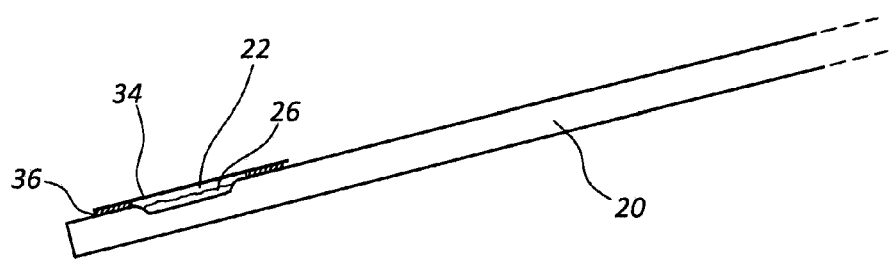
FIG. 8 illustrates a tamping tube for a clot-inducing agent with a cover coupled thereto, in accordance with one embodiment.
Figure 9:
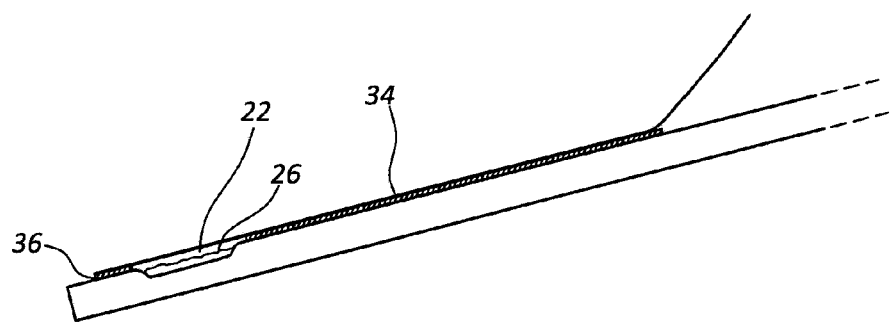
FIG. 9 illustrates the tamping tube of FIG. 8 with the cover being removed, in accordance with one embodiment.

As shown in FIGS. 8 and 9, a cover 34 may be used to maintain the hemostatic, thrombogenic, or clot-inducing agent or substance 26 in place on the tamping tube 20. In the embodiment shown, a clot-inducing agent 26 or thrombogenic substance is provided on a tamping tube 20. The tamping tube 20 includes at least one indentation 22 along a surface thereof. The indentation 22 forms a reservoir for the hemostatic agent 26. A cover 34 is provided over the indentation 22 to keep the clot-inducing agent 26 in place. In one embodiment, the cover 34 is adhesively coupled to the tamping tube 20. Thus, as shown, an adhesive 36 couples the cover 34 to the tamping tube 20. Any suitable manner of coupling the cover to the tamping tube may be used including any suitable adhesive (glues, epoxies, etc.) thermo welding, or other so long as the cover 34 is removable after coupling. FIG. 8 illustrates the tamping tube 20 with a cover 34 coupled thereto. In the embodiment of FIG. 8, the cover 34 spans only a portion of the tamping 20 covering the indentation 22. When it is desired to dispense the hemostatic agent, the user peels back or otherwise removes the cover 34 from the tamping tube 20 or from the portion of the tamping tube 20 housing the clot-inducing agent 26 (thus, the indentation 22), as shown in FIG. 9. In the embodiment of FIG. 9, the cover 34 spans substantially the entire length of the tamping tube 20.

Referring again to FIG. 1, in practice, the carrier tube 504 of the closure device 500 (containing the closure elements described above) is inserted into an insertion sheath 524, which is already inserted within the artery 514. As the closure device 500 and the associated closure elements are inserted into the insertion sheath 524, the anchor 506 passes through and out of a distal end 509 of the insertion sheath 524 and is inserted into the artery lumen 516. The anchor 506 is initially arranged substantially parallel with the carrier tube 504 to facilitate insertion of the anchor 506 through the percutaneous incision 501 and into the lumen 516.

The closure device 500 is then withdrawn from the insertion sheath 524 until the anchor 506 catches on the distal end 509 of the insertion sheath 524 and rotates to the position shown in FIG. 1. When resistance to further retraction of the closure device 500 is felt by an operator, the closure device 500 and the insertion sheath 524 are withdrawn together, causing the anchor 506 to anchor itself within the artery 514 against the artery wall 511. With the anchor 506 anchored within the artery 514 at the puncture site 513, further retraction of the closure device 500 and insertion sheath 524 causes the sealing plug 510 to withdraw from the distal end 507 of the carrier tube 504, thereby depositing the plug within the incision or puncture tract 501.

The closure device 500 drives the tamping tube 505 toward the sealing plug 510 automatically upon withdrawal of the closure device 500 from the puncture tract, tamping the plug toward the anchor 506. Therefore, the sealing plug 510 is tamped while the carrier tube 504 is still arranged adjacent to the puncture 513 in the femoral artery 514, reducing or eliminating any gaps that may otherwise occur between the sealing plug 510 and the puncture 513 in the femoral artery 514.

With reference to the embodiments of FIGS. 4 and 5, as the tamping tube 505 (such as the tamping tube 20 of FIGS. 4 and 5) extends distally from the carrier tube 504 to tamp the plug 510, the indentation 22 having the hemostatic, thrombogenic, or clot-inducing agent or substance 26 is exposed. Thus, the hemostatic agent 26 is automatically released as a function of tamping.

With reference to the embodiments of FIGS. 6 and 7, the tamping tube 505 (such as the tamping tube 20 of FIGS. 6 and 7) may be provided with a retractable sheath 32. After the tamping tube 505 has tamped the plug 510, the retractable sheath 32 may be withdrawn proximally to expose the indentation 22 having the hemostatic, thrombogenic, or clot-inducing agent or substance 26. Thus, the user controls when and if the hemostatic agent 26 is released.

With reference to the embodiments of FIGS. 8 and 9, the tamping tube 505 (such as the tamping tube 20 of FIGS. 8 and 9) may be provided with a removable or peelable cover 34. After the tamping tube 505 has tamped the plug 510, the cover 34 may be removed to expose the indentation 22 having the hemostatic, thrombogenic, or clot-inducing agent or substance 26. Thus, the user controls when and if the hemostatic agent 26 is released.

Figure 10:
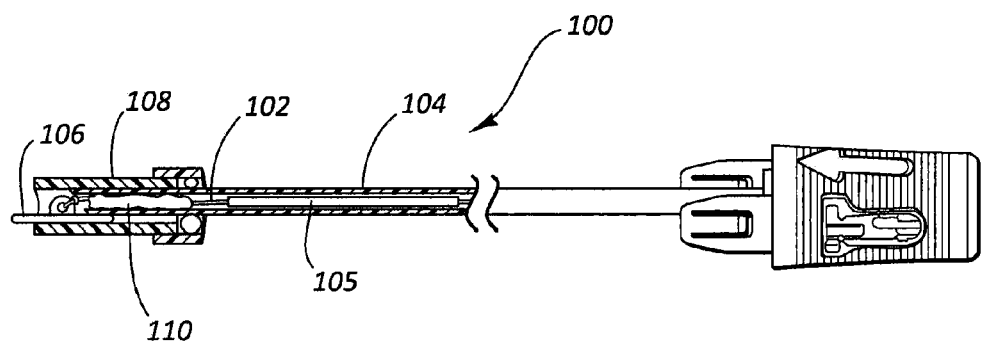
FIG. 10 illustrates a tissue puncture closure device with manual tamping.
Figure 11:
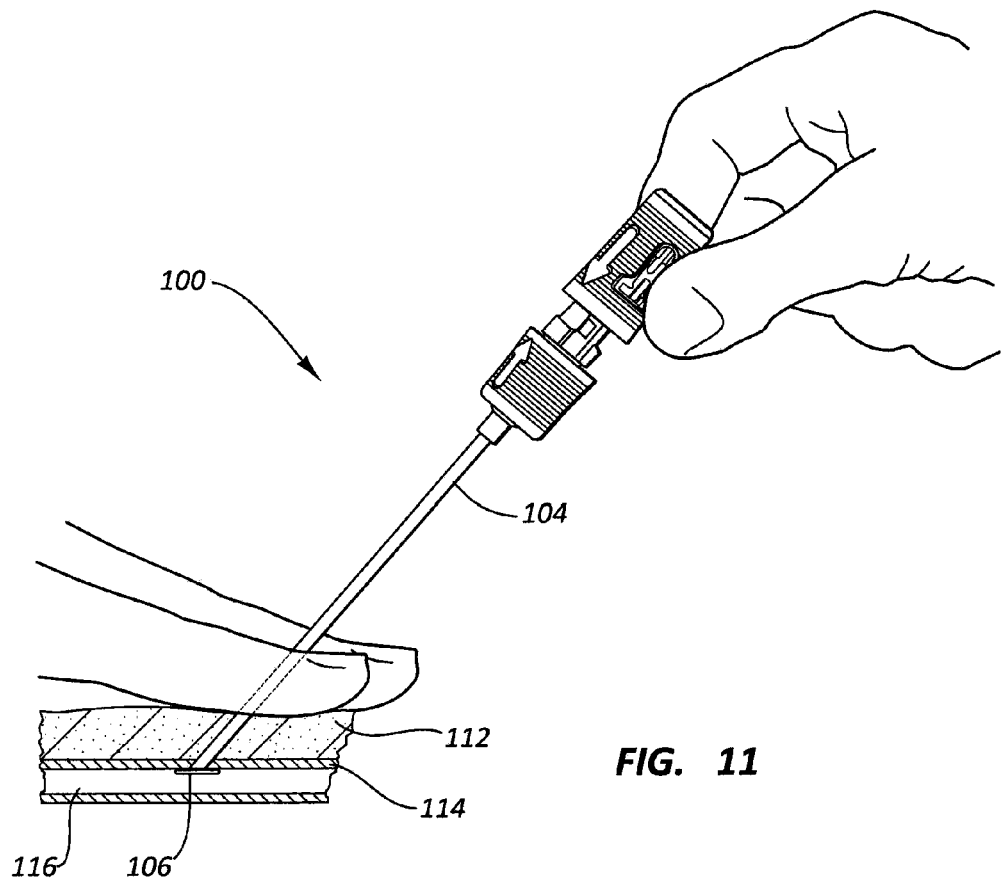
FIG. 11 illustrates an alternative view of the tissue puncture closure device of FIG. 10.

While the methods and apparatuses to promote hemostasis are described with reference to the vascular closure device of FIG. 1, it is to be understood that such reference is made only for the purposes of description. For example, FIG. 1 illustrates a vascular closure device 500 with an automatic tamping mechanism. The vascular closure device may alternatively require manual tamping. The methods and apparatuses may be used with any suitable closure device. FIGS. 10 and 11 illustrates another tissue puncture closure device 100 suitable for use with the present invention. The tissue puncture closure device 100 of FIGS. 10 and 11 employs manual tamping. The tissue puncture closure device 100 includes a suture 102 pre-threaded down through an elongated carrier tube 104 and a tamping tube 105. The suture 102 extends through a collagen sponge 110, then through an anchor 106 located exterior to a distal end 108 of the carrier tube 104 and back into the carrier tube 104, where it is again attached to the collagen sponge 110 disposed on the suture 102 and within the carrier tube 104. As shown in FIG. 11, the sheath 104 is normally inserted through an incision in a patient's skin 112 and through a puncture in a tissue wall 114 until the anchor 106 is deployed within a luminal cavity 116 of an organ or artery. The collagen sponge 110 remains outside of the luminal cavity 116.

Successful deployment of the collagen sponge 110 to plug the puncture typically requires that the sponge be manually exposed from within the sheath 104 and tamped down to an outer surface 118 of the tissue puncture using the tamping tube 105, while simultaneously pulling on the suture 102 to cinch tight the suture 102 connecting the anchor 106 and collagen sponge 110. Accordingly, the sheath 104 is withdrawn from the puncture to expose the collagen sponge 110 and the tamping tube 105. As the suture 102 is pulled and the collagen sponge 110 is tamped with the tamping tube 105, the anchor 106 and the collagen sponge 110 are brought together and held in place with a self-tightening slip-knot on the suture 102. Thus, the tissue puncture is sandwiched between the anchor 106 and collagen sponge 110, thereby sealing the tissue puncture. The suture 102 is then cut and the incision may be closed. The suture 102, anchor 106, and collagen sponge 110 are generally made of resorbable materials and therefore may remain in place while the puncture heals. With reference to the embodiments of FIGS. 4 and 5, as the sheath 104 is withdrawn and the tamping tube 105 (such as the tamping tube 20 of FIGS. 4 and 5) exposed, the indentation 22 having the hemostatic, thrombogenic, or clot-inducing agent or substance 26 is exposed. Thus, the hemostatic agent 26 is automatically released as a function of tamping.

With reference to the embodiments of FIGS. 6 and 7, the tamping tube 105 (such as the tamping tube 20 of FIGS. 6 and 7) may be provided with a retractable sheath 32. After the tamping tube 105 has tamped the collagen sponge 110, the retractable sheath 32 may be withdrawn proximally to expose the indentation 22 having the hemostatic, thrombogenic, or clot-inducing agent or substance 26. Thus, the user controls when and if the hemostatic agent 26 is released.

With reference to the embodiments of FIGS. 8 and 9, the tamping tube 105 (such as the tamping tube 20 of FIGS. 8 and 9) may be provided with a removable or peelable cover 34. After the tamping tube 105 has tamped the collagen sponge 1 10, the cover 34 may be removed to expose the indentation 22 having the hemostatic, thrombogenic, or clot-inducing agent or substance 26. Thus, the user controls when and if the hemostatic agent 26 is released.

Although the invention has been described with reference to preferred embodiments, persons skilled in the art will recognize that changes may be made in form and detail without departing from the spirit and scope of the invention.

What is claimed is:

1. A tissue puncture closure device for partial insertion into and sealing of an internal tissue wall puncture, the tissue puncture closure device comprising:
    a carrier tube having a proximal end and a distal end;
    a filament extending from the distal end of the carrier tube to the proximal end of the carrier tube;
    an anchor for insertion through the tissue wall puncture attached to the filament, the anchor being disposed proximate the distal end of the carrier tube;
    a sealing plug slidingly attached to the filament, the sealing plug being disposed proximate the distal end of the carrier tube;
    a tamping tube for tamping or cinching the sealing plug toward the second end, the tamping tube being configured for insertion in the carrier tube;
    wherein the tissue puncture closure device further comprises an apparatus for promoting hemostasis comprising an indentation formed on a lateral surface of the tamping tube, the indentation having a reservoir to hold a hemostatic substance during insertion of the puncture closure device and delivery of the hemostatic substance.

2. The tissue puncture closure device of claim 1, wherein the carrier tube is sized for receiving the tamping tube, wherein the indentation is exposed and the hemostatic substance released when the tamping tube extends distally from the carrier tube.

3. The tissue puncture closure device of claim 1, further comprising a hemostatic substance provided with the filament.

4. The tissue puncture closure device of claim 3, wherein the filament is impregnated with the hemostatic substance.

5. The tissue puncture closure device of claim 3, wherein the filament is coated with a hemostatic substance.

6. The tissue puncture closure device of claim 1, further comprising a wiper positioned on the tamping tube generally adjacent the at least one indentation.

7. The tissue puncture closure device of claim 1, wherein the tamping tube is configured for extending distally from the carrier tube in use, thereby exposing the hemostatic substance to the site of the tissue wall puncture.

8. The tissue puncture closure device of claim 1, further comprising a retractable sheath positioned over the tamping tube, the retractable sheath acting as a lid for the indentation and being configured for proximal retraction to expose the hemostatic substance to the site of the tissue wall puncture.

9. The tissue puncture closure device of claim 1, further comprising a cover disposed over the indentation on the tamping tube, the cover being configured for removal to expose the hemostatic substance to the site of the tissue wall puncture.

10. The tissue puncture closure device of claim 9, wherein the cover is adhesively coupled to the tamping tube.

11. The tissue puncture closure device of claim 9, wherein the cover extends over substantially the length of the tube.

12. The tissue puncture closure device of claim 1, wherein the apparatus for promoting hemostasis is configured and positioned such that the hemostatic substance is released proximally of the sealing plug in use.

* * * * *